United States Patent
Autant et al.

[11] Patent Number: 6,022,562
[45] Date of Patent: Feb. 8, 2000

[54] MEDICINAL AND/OR NUTRITIONAL MICROCAPSULES FOR ORAL ADMINISTRATION

[75] Inventors: Pierre Autant, Commentry; Jean-Philippe Selles, Montpellier; Gérard Soula, Meyzieu, all of France

[73] Assignee: Flamel Technologies, Venissieux Cedex, France

[21] Appl. No.: 08/544,208

[22] Filed: Oct. 17, 1995

[30] Foreign Application Priority Data

Oct. 18, 1994 [FR] France .................................. 94 12759

[51] Int. Cl.$^7$ ...................................................... A61K 9/14
[52] U.S. Cl. .......................... 424/489; 424/468; 424/490; 424/478; 424/492; 424/456
[58] Field of Search ...................... 424/489, 490, 424/488

[56] References Cited

U.S. PATENT DOCUMENTS 4,461,759  7/1984  Dunn ........................................ 424/19
5,028,434  7/1991  Barclay et al. .......................... 424/473
5,286,497  2/1994  Hendrickson et al. ................. 424/490

FOREIGN PATENT DOCUMENTS 0 207 041   6/1986   European Pat. Off. .
39 43 242   6/1990   Germany .

*Primary Examiner*—Thurman K. Page
*Assistant Examiner*—William E. Benston, Jr.
*Attorney, Agent, or Firm*—Bacon & Thomas

[57] ABSTRACT

The present invention relates to microcapsules for the oral administration of medicinal and/or nutritional active principles (AP), which are smaller than or equal to 1000 μm in size. These microcapsules consist of particles which are coated with a coating material consisting of a mixture of a film-forming polymer derivative, a hydrophobic plasticizer, a functional agent and a nitrogen-containing polymer. These microcapsules are also characterized by their ability to remain in the small intestine for a long time (at least 5 hours) and to allow, during the residence, release and absorption of the AP. The invention also relates to a process for the production of the said microcapsules.

14 Claims, 4 Drawing Sheets

MEDICINAL AND/OR NUTRITIONAL MICROCAPSULES FOR ORAL ADMINISTRATION

The field of the present invention is that of sustained-release systems for medicinal and/or nutritional active principles (Aps), which are intended for oral administration.

The present invention thus relates to microcapsules intended for oral administration, and containing at least one AP, with the exclusion of acetylsalicylic acid, and which have, in particular, as essential characteristics, a longer residence time in the small intestine than the duration of natural transit, what permits so an increase of the effective in vivo absorption of these APS.

The invention also relates to a process for the preparation of the microcapsules mentioned above.

The pharmaceutical systems to which the present invention more particularly relates are those of the type which allow a sustained (or even controlled) absorption in the small intestine. The present invention does not exclude the use of APs having a possible nonspecific absorption in the stomach and/or the colon.

The advantage of sustained-release systems for the administration of a medicinal product is well known. They make it possible in particular to ensure better cover of the therapeutic need, since the useful plasma concentration of AP may be maintained for longer than in the case of immediate-release forms. Furthermore, they make it possible to prevent, or to limit, the size and the number of AP-excessive concentration peaks in the plasma, thereby decreasing the toxicity of the medicinal product and its side effects. Moreover, these systems make it possible, by virtue of their increased duration of action, to limit the number of daily intakes, thereby decreasing the limitation for the patient and improving the observance of the treatment.

Systems have thus been sought which make it possible to prolong the action of a medicinal product, and numerous references exist relating to this objective. Formes Pharmaceutiques Nouvelles, BURI, PUISIEUX, DOELKER et BENOIT, Lavoisier 1985, pl75–227 may advantageously be consulted in this respect.

The prior art describes, for example, attempts directed towards producing sustained-release systems, with the aim of providing medicinal forms, for example forms to be taken once a day.

Monolithic systems have thus been proposed, such as tablets, in which the dose to be administered is in the form of a solid object. Thus, DE Patent Application No. 39 43 242 (FR No. 2 670 112) discloses "matrix" type granules comprising AP particles, eventually with inert excipent(s), useful for making tablets. Each granule consists of a multitude of said particles included in a roughly spherical matrix comprising a cellulosic polymer, a vinylic or acrylic polymer, a plasticizer and a lubricating agent. These granules are pharmaceutical forms defined in the pharmacopoeia. They are clearly distinct from microcapsules, which are also defined in the pharmacopoeia. Moreover, these granules are used to make monolithic tablets, whose numerous drawbacks will be described hereinafter. In addition, these tabletting granules have a size superior or equal to 1,2 mm. The matrix of the granules described in the examples of the DE-A-39 43 242, always comprises one polyacrylate and one cellulosic polymer, this latter being present in a low proportion, inferior to 50% by dry weight with respect to all the components of the matrix. Moreover, this application teaches that, to obtain bioadhesivity, the granules' matrix has to contain a significative larger amount of acrylate polymer than cellulosic polymer. And in any case, there is no reason that these granules stay in the small intestine during a time superior to the natural gastrointestinal transit time. Besides, this feature is neither disclosed nor suggested in the DE application.

Several tablets are also known which are film-coated with a coating material of, for example, cellulosic, acrylic, starch, polyethylene glycol or gum type, or analogues of these products. This coating allows tablets both to be resistant to physiological fluids and, likewise, to protect sensitive APs in these media in order to increase, in fine, the bioavailability of the APs, and also to prolong the release of the said APs.

Thus, U.S. Pat. No. 4,461,759 describes a coated tablet which protects the AP from the harmful effects of the stomachal acidity and having the presumed property of releasing at a constant rate in the gastrointestinal tract. Indeed, none deconvolution analysis has been done, thus this property is not established.

Another example of a monolithic tabletted form is that consisting in using a microporous film coating which allows the release of the AP under the effect of an osmotic pressure. This sustained release takes place irrespective of the solubility of the AP in the medium. This embodiment is described in patent application WO 91/16885 and in U.S. Pat. No. 5,028,434.

These film-coated monolithic systems have limited possibilities of use for various reasons. Firstly, in these systems, the dose of medicinal product is provided as a single physical entity, which presents the risk of release of a large amount of AP, either by chewing when it is taken or by breaking of the film coating during gastrointestinal transit, thereby disrupting their therapeutic effectiveness and presenting risks of serious side effects. Furthermore, taking their large size into account, these systems can only leave the stomach when the pylorus is open. Now, opening of the pylorus occurs sequentially and as a function of feeding. Consequently, the residence time of monolithic systems in the stomach varies enormously as a function of the time, the volume and the nature of meals, and also varies from person to person. These systems thus have a wide variability of absorption, or even of bioavailability, depending on the individual and the time at which they are taken. Moreover, their residence time in the small intestine is subject to natural transit, and these forms rapidly end up in the colon, where their release is completed. However, absorption by the colon is poor for a large number of APs. In addition, it is very irregular, given the high viscosity of the medium, the low surface area of the colon mucosa and the wide variability in transit time at this level. Thus, it is well known for these systems, that the sustained-release is not synonymous with a sustained-absorption, beyond natural transit time in the small intestine.

In order to avoid the pitfalls inherent in monolithic systems, multiparticulate forms have been proposed in which the constituent elements have an individual mean size generally of less than 2 mm. This size makes it possible to cross the stomach independently of the opening of the pylorus. The gastric transit time is thus shorter and above all more uniform. In practice, these multiparticulate forms are essentially administered in the form of gelatin capsules or tablets which may rapidly be broken down.

The prior technical literature abounds with descriptions of microparticulate pharmaceutical systems giving a sustained release of AP.

For example, Patent EP 396,425 discloses a system intended for the administration in a single daily dose of AP such as nitrates, ephedrines and potassium chloride. To this end, the AP is bound to the surface of inert spherules with a diameter ranging from 250 to 2000 microns, using a known binder. The particles are then film-coated with a cellulose compound and a plasticizer, these being intended to slow down the release of the AP. These film-coated particles are generally used as a mixture with uncoated particles intended to provide an initial dose which is released immediately into the body. The in vitro dissolution trials show that the AP is released over about 24 hours, but no measurement of bioavailability is performed in vivo. This application does not make mention of a prolongation of the transit time and of in vivo absorption in the small intestine. U.S. Pat. No. 5,286,497 describes a formulation based on Diltiazem (AP) which is designed to be taken once a day. To this end, the system is obtained by mixing two types of particles containing Diltiazem. The AP is bound to the surface of inert granules of sugar or of starch, which are then optionally film-coated. It has a maximum Diltiazem content of the order of 45% of the weight of the final form. In this medicinal form, particles of a first type give rapid release and provide a first stage of the therapeutic cover, whereas particles of the second type are of delayed action and only start their actual release after the end of the action of the particles of the first type. Besides its low content of AP, this system has the drawback of requiring the preparation and mixing together of two types of particles, thereby complicating the manufacturing process and placing a strain on its cost price. Moreover, this system which provides two successive doses of AP is adapted to the specific case of Diltiazem. This product is an AP which undergoes considerable degradation during the first passage through the liver. In addition, that patent does not make mention of a prolonged time of residence and absorption in the small intestine, and the particles of the system which form the subject of that patent are subject to natural gastrointestinal transit. Furthermore, the dose contained in the particles of the 2nd type with delayed action, and which begin their release about 12 hours after ingestion, is delivered to and absorbed in the colon. Finally, the fact that the first type particles give rapid release, can involve high plasmatic peaks detrimental to a good tolerance.

Diltiazem moreover has a long half-life in the body, of the order of 6 hours. In this case, the plasma concentration maintains itself naturally above the effectiveness threshold long enough to allow the ready production of a form taken in a single daily dose. This is exploited by EP 0,315,197, which also describes a form of Diltiazem taken in a single daily dose, which is capable of maintaining the plasma level for 24 hours, by means of a tablet which releases, in 5 hours, 90% of a dose of between 90 and 270 µg.

When the AP has a high rate of absorption, or a slow rate of biological removal, its plasma half-life is naturally long, and a medicinal product with sustained action is easy to prepare. However, the same cannot be said for the preparation of a medicinal product based on an AP with a short plasma half-life, for example of less than 3 hours. The reason for this is that such an AP must be made available in the body as and when it is used.

Consequently, the short residence time in the small intestine poses a considerable problem to those skilled in the art interested in developing sustained-absorption medicinal products intended for oral administration. The medicinal product administered orally is, in effect, subject to the natural transit of the gastrointestinal tract, thereby limiting its residence time. Now, the small intestine is the preferred location for systemic absorption and it represents the ideal site for making APs available. Thus, it is easy to appreciate the value of a pharmaceutical form having an increased residence time in the small intestine, in view of the sustained in vivo absorption of an AP, beyond normal transit time in the small intestine.

Many studies have been performed regarding the time for gastrointestinal transit. These studies show that the duration of gastric transit is very variable, in particular as a function of feeding, and that it is between a few minutes and a few hours. On the other hand, the duration of transit in the small intestine is particularly constant and, more precisely, is 3 hours plus or minus one hour (see for example S. S. DAVIS: Assessment of gastrointestinal transit and drug absorption, in Noval drug delivery and its therapeutic application, Ed L. F. PRESCOTT- W. S. NIMMO, 1989, J. WILEY & SON, p. 89–101).

Now, as indicated above, it would be advantageous, in a great many cases, to be able to deliver the APs to the small intestine, which is the preferred location for systemic absorption. The ideal residence time for a sustained-release system intended for the majority of APs, including those having a very short plasma half-life, would consequently be longer than 5 hours, preferably longer than 7 hours and, for example, between 8 and 24 hours, thereby allowing the entire 24-hour period to be covered.

The advantage of a system having a residence time in the small intestine of the order of 8 to 24 hours, and thus affording sustained release and absorption (of at least 90% of the dose) throughout all or for part of this period, would be manifold:

firstly, by assuring the release of a dose of AP at an optimum flow, it would make it possible to improve the bioavailability thereof and to limit the dose thereof to be administered, furthermore, it would make it possible to obtain sustained plasmatic concentrations for APs which have a short plasma half-life. This would optimize the number of daily intakes and in particular the preparation of systems to be taken once a day for a larger number of APs. The production of such forms would thus only be limited by the volume of the dose to be administered, which must remain acceptable for the patient.

Pharmaceutical forms for oral administration have been produced with the intention of artificially increasing their residence time in the gastrointestinal tract. The aim of such forms is an intrinsic transit, independent of natural transit.

The literature describes in particular so-called floating tablets, characterized by a long residence time in the stomach. For example, U.S. Pat. No. 4,869,908 describes such a system. This system is more particularly suited to the administration of APs having a preferential absorption at the gastric level, which is very limiting.

Other research efforts have also been made with the same aim of increasing the transit time, but for microparticulate systems.

Patent FR 2,395,026 claims a process for the preparation of a system in which the microparticles containing the AP are in a sustained-release form containing, in their composition, a densifying agent which allows a significant prolongation in the transit time, which may then exceed 24 hours. This system was developed after observation of the fact that transit in the small intestine is slowed down considerably when the density of the particles exceeds 1.4 grams per cubic centimeter. The same approach of increasing the transit time by elevation of the density is adopted in EP applications 0,080,341 and 0,173,210. However, such systems have the drawback of requiring the introduction of a large amount of densifying agent, of the order of 30 to 80% of the total weight of the form, which limits the content of AP in the system and constitutes a handicap for the manufacture of forms requiring a large dose of AP.

Another approach for prolonging the transit time consists of the development of bioadhesive systems.

Thus, patent EP 0,452,268 claims a bucco-adhesive system in the form of microparticles film-coated with a gel of xanthan/carob gums or with ethylcellulose. The effectiveness of such a system, essentially intended for the mouth, is not established, and all the less so since the particles are coated with a film of wax as an outer layer, which is intended to sustain their release but which makes adhesion improbable, and anyway not demonstrated in vivo.

Application EP 0,516,141 is directed towards the development of a bioadhesive particulate system by overcoating, of any given sustained-release form of an AP, with an adhesive composition based on polymers such as water-soluble derivatives of cellulose, acrylic polymers known under the trade names Carbopol® or Polycarbophil®, alginates, gelatin or pectin. That invention thus proposes, in the systems in question, to separate two essential functions, namely the control of the release of the AP, on the one hand, and the bioadhesion, on the other. However, the validation tests for such a form are limited to ex vivo tests and have not demonstrated a sustained absorption in vivo.

Many authors have studied potentially bioadhesive substances such as carboxymethylcellulose, polyacrylic acid, Carbopol®, Polycarbophil®, gelatin and other natural or synthetic polymers. These substances are described and assessed, for example, by D. DUCHENE et al., Pharmaceutical and medical aspects of bioadhesive systems for drug administration, in Drug. Dev. Ind. Pharm. 14 (2 & 3), 283–318(1988) and J. M. GU et al., Binding of acrylic polymers to mucin/epithelial surfaces, structure-property relationships, in CRC Crit. Rev. in Therap. Drug. Carrier Syst., Vol.5, Issue 1 (1988). It was found that certain polymers have adhesive properties with regard to certain mucous membranes, for example oral or vaginal mucous membranes. However, in general, no bioadhesion is established in vivo in the small intestine, for these substances, and/or for the existing orally-administered forms. No evidence in support of the adhesion in the small intestine is in fact provided, either by direct observation or by a pharmacokinetic study establishing a prolonged residence time therein objectified by a sustained in vivo absorption. In this respect, A. J. MOËS - Gastroretentive dosage forms, in Crit. Rev. Ther Drug Carrier Syst. 10 (2) 143–195 (1993) and A. T. FLORENCE - Drug Delivery: Advances and Commercial Opportunities in Connect Pharma LTD p 40–44 may be consulted, for example.

It should, however, be noted that the polymers having (by far) the best bioadhesion according to the in vitro or ex vivo tests described in the literature are essentially the acrylic and methacrylic acid derivatives.

A review of the prior art reveals a large number of unsuccessful attempts directed towards providing a general solution to the prolonged retention and sustained release of AP in the small intestine, for periods which may be up to 24 hours in the case of oral administrations. Furthermore, none of the prior art takes account of the set of constraints inherent in the production of a multifunctional system which may be applied to the majority of APs, and no satisfactory solution is available to date.

Indeed, there are a large number of constraints opposing the production of such a system, and there are many difficulties to be solved.

Some of these constraints and difficulties are outlined below:

it is advantageous for the system to have rapid and uniform transit in the stomach, in order to ensure reproducibility of the therapeutic effect within the same person and from person to person, it is advantageous for the system to remain in the small intestine throughout the period required for absorption of the dose, in particular for APs having a short elimination half-life ; it is thus preferable for the system to reside in the small intestine for a period which is considerably longer than the time of natural transit, it is preferable for the system to be able to have a high content of AP in order to allow the medicinal product to be prepared, even when the dose of AP is large, while at the same time respecting the patient's comfort, it is preferable for the system to be able to avoid the risk of a massive absorption into the body of all, or of a large fraction, of the dose normally intended to cover a long period, it is desirable for the system not to allow the release of a large amount of AP, for a prolonged period at a localized level of the gastrointestinal mucous membranes, in order to avoid the risks of ulceration, it is preferable for the system to have sufficient mechanical strength to allow the gradual absorption of the AP, according to a determined and reproducible profile, until the dose is fully depleted, it is desirable for the system to protect the AP as well as possible against possible attack from physiological media during its residence in the body, it is advantageous that the system be unsensitive to pH variations in the gastrointestinal tract, in order to safeguard the regularity of the AP availability, lastly, it is desirable for such a system to be able to be manufactured in a simple and economical manner.

In this context, the observation cannot be avoided that there is a shortcoming in a pharmaceutical system for oral administration of the AP, which possesses, cumulatively and for a wide range of APs, the following specifications inter alia:

rapid and uniform transit in the stomach reflecting the absence of a long time in the in vivo absorption profile, independent of the gastric activity, slow transit in the small intestine, reflecting by a in vivo absorption profile on a period considerably longer than that of natural transit (3 h±1), gradual release of the AP until the dose is fully depleted (>90%), absence of irritation of the mucous membranes, high content of AP, reduced cost price.

One of the essential aims of the present invention is to remedy this shortcoming.

To this end, the subject of the present invention is a pharmaceutical system formed of microcapsules of reservoir kind containing at least one medicinal and/or nutritional Active Principle (AP) with the exclusion of acetylsalicylic acid (ASA), which are intended for oral administration, characterized:

in that they consist of particles of AP each coated with at least one coating film of specific following composition:

1- at least one film-forming polymer (PI) which is insoluble in the liquids of the digestive tract, present in a quantity of 50 to 90%, preferably 50 to 80% by weight of dry matter of the whole coating composition, and consisting of at least one non-hydrosoluble cellulose derivate, ethylcellulose and/or cellulose acetate being prefered;

2- at least one nitrogen-containing polymer (P2), present in a quantity of 2 to 25, preferably 5 to 15% by weight of dry matter of the whole coating composition, and consisting of at least one polyacrylamide and/or one poly-N-vinylaride and/or one poly-N-vinyl-lactame, the polyacrylamide and/or the polyvinylpyrrolidone being prefered;

3- at least one plasticizer present in a quantity of 2 to 20%, preferably 4 to 15% by weight of dry matter of the whole coating composition, and consisting of at least one of the following compounds:glycerol esters, phtalates, citrates, sebacates, cetylalcohol esters, castor oil and cutin, castor oil being particularly prefered;

4- at least one surface-active and/or lubricating agent, present in a quantity of 2 to 20%, preferably 4 to 15% by weight of dry matter of the whole coating composition, and chosen from anionic surfactants, preferably the alkali metal or alkakine-earth metal salts of fatty acids, stearic acid and/or oleic acid being preferred, and/or from nonionic surfactants, preferably polyoxyethylenated esters of sorbitan and/or polyoxyethylenated esters of sorbitan and/or polyoxyethylenated derivatives of castor oil, and/or from lubricants such as stearates, preferably calcium, magnesium, aluminium or zinc stearate, or such as stearylfumarate, preferably sodium stearylfumarate, and/or glyceryl behenate, said agent comprising only one or a mixture of the above products;

in that they have a particle size of between 50 and 1 000 microns, preferably of between 100 and 750 microns and, more preferably, of between 100 and 500 microns;

in that they are designed so as to be able to remain in the small intestine for a period of at least about 5 hours, preferably of at least about 7 hours and, even more preferably, for a period of between about 8 hours and about 24 hours, and permitting so the absorption of the AP during at least part of their residence in the small intestine.

The Applicant Company has, to its credit, in an entirely surprising and unexpected manner, developed such a pharmaceutical system.

The present invention thus discloses a novel sustained-release system which has, among other essential and simultaneous characteristics, a reduced residence time in the stomach and a duration of transit in the small intestine which is considerably longer than the duration of natural transit. In particular, the sustained-release system according to the invention has a residence time in the small intestine of between 5 and 24 hours, that is to say one which is 2 to 12 times longer than the time for natural transit. The AP absorption is naturally linked to its release out of the microcapsules.

For a given AP, the long residence time can be demonstrated through the measurement of a in vivo absorption time, largely superior to the natural transit time in the small intestine. Such a measurement is given by the plasmatic concentration of the AP, is a reliable and admitted mean to make objective the residence time.

The system claimed also makes it possible, independently of this long residence time, to ensure the sustained release of the APs used according to the present invention. It should be noted that the presence of the system for a period of the order of 24 hours in the small intestine does not in any way impose a continuous release throughout this period. Those skilled in the art will know how to modify the duration of release to within a time interval which is suited to the specific AP in question, taking into account the pharmacological aim.

The present invention gives access in particular to oral pharmaceutical forms, containing single daily doses, for a larger number of APs than the pharmaceutical forms according to the prior art.

In the account of the invention, mention will be made of the term "microcapsulese", which denotes film-coated particles and distinguishes them from the particles of non-film-coated AP, which will be referred to as "microparticles".

The coating film is advantageously of sufficient mechanical strength to prevent it breaking and/or splitting in the body, up to the end of the release of the active principle. This ability of the film to retain its physical integrity even after complete elution of the AP is observed, in particular, for coating thicknesses of between 2 and 100 microns.

These microcapsules may be likened to vehicles which allow the transport and release of one or more APs in the small intestine.

The microcapsules preferably comprise an amount of AP of between 55 and 95% by weight, and preferably of between 60 and 85% by weight.

It is important to note that this functionality of prolonged residence time in the small intestine is not acquired to the detriment of the other specifications required for a pharmaceutical system of the type described in the present invention. In particular, the system has sufficient flexibility in its composition to be able to be adapted to sustained absorption, during periods ranging from 5 to 24 hours, for example, for a large number of APs having solubilities of between a few milligrams and a few hundred grams per liter.

Another consideration to bring to the number of advantages of the microcapsules according to the invention is that even in the case of prolonged adhesion to the gastrointestinal mucous membranes, there is no risk of ulceration. The reason for this is that, given their small particle size, each microcapsule contains only a fraction of the AP, typically representing from $1/15,000$ to $1/150,000$ of the dose administered, which is very different from the case of the monolithic systems discussed above.

Moreover, this small particle size is in itself a factor which allows great uniformity of transit; gastric transit then being, as has been seen, independent of opening of the pylorus and, consequently, particularly rapid.

Another subject of the present invention is a process for the production in particular of the microcapsules according to the invention as defined above, the said process consisting essentially in:

a) selecting or in case of need making microparticles of AP with a particle size of between 50 and 1000 microns, preferably of between 100 and 750 microns and, even more preferably, of between 100 and 500 microns, b) preparing a coating composition by mixing together a polymer P1, a polymer P2, a plasticizer and a surface-active and/or lubricating agent in a solvent system, c) applying the mixture obtained in b) to the surface of the microparticles of AP, d) drying the microcapsules thus obtained, and e) optionally, mixing these microcapsules with at least one anti-agglomerating agent.

Such a methodology is one of the advantageous general methodologies which allow the microcapsules of the invention to be produced in a simple and economical manner.

DETAILED DESCRIPTION OF THE INVENTION

Figure 1:
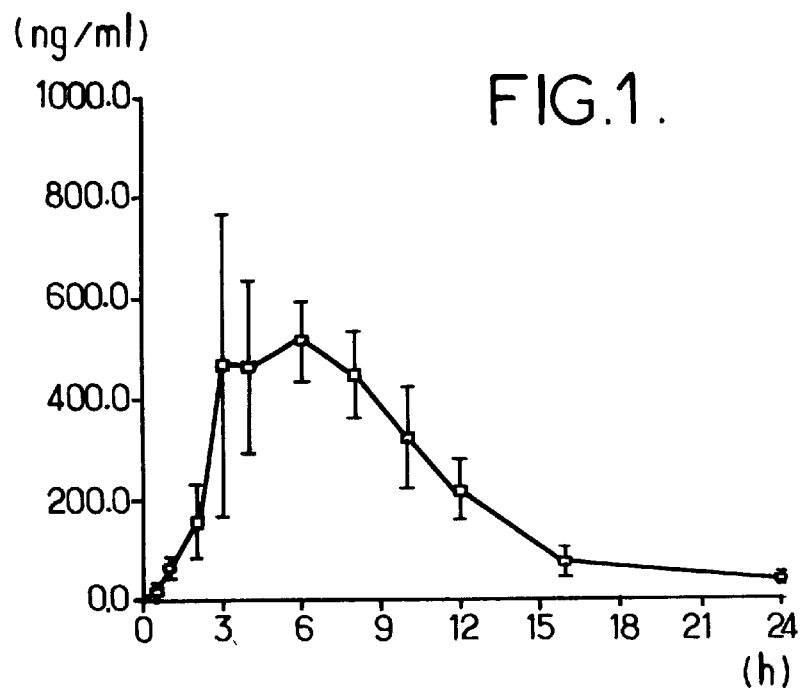
FIG. 1 represents the graph of the atenolol plasma concentrations (ng/ml) as a function of time in hours (h) after the swallowing of the atenolol (100 mg) microcapsules (example 1).

It can readily be understood that the description of some of the essential parameters of the invention, which are the residence time of the microcapsules of AP in the small intestine and the in vivo absorption of the AP, is relatively difficult if it is approached directly. Thus, an alternative which may be considered is to define the residence time in the small intestine of microcapsules, administered orally, as well as the in vivo absorption by means of measurement of the plasma concentration of an AP which has a short half-life in the body and which is not absorbed in the colon.

Now, it is seen that in this respect, atenolol, cimetidin and aciclovir constitute preferred tracers, since they are not absorbed in the colon and since their half-lifes are respectively. 2 h, 5 h and 1,5 h.

This will be illustrated by the examples.

These microcapsules find one part of their singularity in their reservoir structure clearly distinct of matrix type systems (cf article of C. DUVERNEY and J. P. BENOIT in "L'actualitéchimique", Dec. 86, and cf. book intitulated "Novel drug delivery and its therapeutic application" L. F. PRESCOTT & W. S. NIMMO, Ed. John WILEY & Sons).

The particle size of the microcapsules is one of the important rameters of the invention. This particle size is determined by screening. In actice, the particle size is, for example, between 100 and 500 microns for the microcapsules according to the invention.

The coating film of the microparticles obviously forms one of the main components of the present invention.

This coating composition is an original and non-arbitrary choice of four compounds whose functionalities combine themselves to produce the surprising characteristics aimed by the invention.

Ethylcellulose and cellulose acetate which can be film-forming polymer P1 are soluble in at least one organic solvent of boiling point between 35 and 120° C.

Polyvinylpyrrolidone and/or polyacrylamide representing P2 are polymers soluble in at least one solvent for P1.

The plasticizer and the surface-active and/or lubricating agent that are more particularly preferred are, respectively, on the one hand, castor oil, and/or diethyl phthalate, and/or triethyl citrate and/or salicylic acid, and on the other hand, magnesium stearate, and/or sodium oleate and/or polyoxyethylenated sorbitan laurate.

As an example of a coating composition more readily used, there may be mentioned that comprising: ethylcellulose (P1)/polyvinylpyrrolidone (P2)/castor oil (plasticizer)/magnesium stearate (lubricating agent), which are respectively present in the following preferred relative contents: 60–80%/5–10%/5–10%/2–8%, the percentages being given by weight relative to the total of the components of the coating.

This coating composition constitutes one of the original specificities of the present invention. It is characterized by an intimate combination of the four compounds mentioned above. Naturally, it is possible to add thereto adjuvants conventionally used in the field of film-formation, such as pigments or fillers.

In order to prevent the problems of caking of the coated particles constituting the microcapsules of the invention, provision is advantageously made to add thereto at least one anti-agglomerating agent formed, preferably, of talc, colloidal silica or of a mixture of the two. This addition occurs, for example, in amounts of from 0,5 to 5% by weight, preferably of from 1,5 to 3% by weight.

The APs used for the preparation of controlled-release systems according to the present invention may be chosen, with the exclusion of acetylsalicylic acid, from at least one of the following wide varieties of active substances, e.g.: antiulcer, antidiabetic, anticoagulant, antithrombic, hypolipaemic, antiarrhythmic, vasodilatory, antianginal, antihypertensive, and vasoprotective agents, fertility enhancers, labour inducers and inhibitors, and contraceptive, antibiotic, antifungal, antiviral, anticancer, anti-inflammatory, analgesic, antiepileptic, antiparkinsonian, neuroleptic, hypnotic, anxiolytic, psychostimulatory, antimigraine, antidepressant, antitussive, antihistamine or anti-allergic agents.

When it is medicinal, the AP is preferably chosen from the following compounds: pentoxifyllin, prazosin, acyclovir, nifedipin, diltiazem, naproxen, ibuprofen, flurbiprofen, ketoprofen, fenoprofen, indomethacin, diclofenac, fentiazac, oestradiol valerate, metoprolol, sulpiride, captopril, cimetidin, zidovudin, nicardipin, terfenadin, atenolol, salbutamol, carbamazepin, ranitidine, enalapril, simvastatin, fluoxetin, alprazolam, famotidin, ganciclovir, famiciclovir, spironolacton, 5-asa, quinidin, perindopril, morphin, pentazocin, paracetamol, omeprazol, metoclopramid and mixtures thereof.

The active principles to which the present invention also relates may be chosen from nutritional and/or dietary supplements or mixtures thereof, such as, for example, vitamins, amino acids, antioxidants, trace elements or mixtures thereof.

In general, the particles of AP according to the invention are coated by spraying with the intimate combination forming the coating film, as a dispersion or a suspension in an organic solvent or a mixture of organic solvents.

The coating process, which constitutes another subject of the invention, falls within the scope of micro-encapsulation techniques, the principles of which are summarized in the article by C. DUVERNEY and J. P. BENOIT in "L'actualité chimique" December 1986. More precisely, the technique considered is microencapsulation by film formation, which permits to obtain "reservoir" systems versus matrix systems.

This process preferably consists essentially in:

a) selecting, or in case of need making, microparticles of AP with a particle size of between 50 and 1000 microns, preferably of between 100 and 750 microns and, more preferably, of between 100 and 500 microns, b) preparing the coating composition by mixing together a polymer P1, a polymer P2, the plasticizer and the surface-active and/or lubricating agent in a solvent system, c) applying the coating composition/solvent system mixture to particles of AP, d) drying the microcapsules thus obtained, and e) optionally, mixing these microcapsules with at least one antiagglomerating agent.

The solvents suitable for use in the composition of the solvent system are, for example, ketones, esters, chlorinated solvents, alcohols, which are preferably aliphatic, alkanes or mixtures thereof These solvents are advantageously $C_1$–$C_6$ compounds, given that acetone, methyl ethyl ketone, methanol, ethanol, isopropanol, cyclohexane and methylene chloride are particularly preferred.

In order to go into greater detail into the coating methodology which may be used in accordance with the invention, it may be pointed out that the coating composition/solvent system mixture is applied by spraying onto the particles of AP set in motion, preferably by mechanical stirring or by fluidization.

In order to obtain microcapsules according to the invention, it is necessary to encapsulate particles of AP of size between 50 and 1000 microns, preferably between 100 and 750 microns and more preferably between 100 and 500 microns.

The particles of AP, of desired particle size and necessary for the production of microcapsules according to the invention, may be crystals of pure AP and/or AP which has undergone a pretreatment by one of the conventional techniques of the art such as, for example, granulation in the presence of a small amount of at least one standard binder and/or of an agent modifying the intrinsec solubility feature of the AP.

According to an advantageous embodiment of the invention, the content of AP of the particles before coating is between 75 and 100% by weight, preferably between 95 and 100% by weight.

The amount of coating agent in the microcapsules represents from 5 to 40% of the weight of the coated microcapsules.

The actual density of the microcapsules according to the invention is not critical, but is preferably between 1.0 and 1.35 grams per cubic centimeter.

According to a preferred embodiment of the process, in accordance with the invention, for the micro-encapsulation of particles of AP, the following steps are provided for:

$a_1$/preparation, firstly, of a mixture comprising from 70 to 80% by weight of a film-forming polymer P1 and 5 to 10% by weight of a plasticizer for 5 to 10% by weight of a nitrogen-containing polymer P2 in solution, either in an acetone/alkanol mixture such that the acetone/alkanol volume ratio is between 50/50 and 70/30, or in a solvent chosen from cyclohexane, toluene, carbon tetrachloride, chloroform and methylene chloride, $a_2$/placing in suspension, in the solution prepared in the above step, of 2 to 8% by weight of surface-active and/or lubricating, b/ spraying of the resulting mixture onto the microparticles of active principle, in a fluidized bed, c/ drying of the microcapsules after the spraying, in a fluidized bed and/or in the oven, d/ mixing of the microcapsules thus obtained with 0.5 to 3% by weight of anti-adhesion agent, on the basis of 100% of final product obtained after mixing.

The microcapsules described above, and possibly obtained by the process which is also outlined above, may be used for the manufacture of novel pharmaceutical or nutritional preparations of various APs, having optimized therapeutic or nutritional performance and preferably provided in the form of tablets that can advantageously be crumbled, or powders or gelatin capsules. Thus the invention concerns new galenical systems (tablets, powders, gelatin capsules) containing said microcapsules.

These microcapsules are all the more advantageous since they are also perfectly tolerated by the body, in particular at the gastric level, and they may moreover be obtained in a simple and economical manner.

The present invention also relates to these novel pharmaceutical or dietetical preparations as such, which are of original structure, their presentation and their composition. Such pharmaceutical or nutritional preparations are administered orally, preferably by single daily doses.

It should be noted that it may be advantageous to mix within the same gelatin capsule, the same tablet or the same powder, at least two types of microcapsules which have release kinetics that are different but are within the characteristic scope of the invention.

The microcapsules according to the invention may also be mixed with a certain amount of AP which is immediately available to the body.

Another subject of the invention is the use of microcapsules as vehicles for at least one medicinal and/or nutritional Active Principle (AP) capable of residing in the small intestine for a prolonged period, the said microcapsules:

Δ being designed for oral administration and:

to be able to reside in the small intestine for at least about 5 hours, preferably at least about 7 hours and, even more preferably, for a period of between 8 and 24 hours, to allow the release of the AP in the small intestine for at least part of their residence time, Δ and consisting of particles of AP each coated with at least one coating film of specific composition and having a particle size of between 50 and 1000 μm, preferably of between 100 and 750 μm and, even more preferably, of between 100 and 500 μm.

Another subject of the invention is a method of treating and/or preventing diseases and/or pains consisting in using the microcapsules as above described.

The invention will be better explained by the examples below, which are given purely by way of illustration and allow the invention to be clearly understood and allow the production and/or implementation variants thereof to emerge, as well as the various advantages thereof.

EXAMPLES

MAKING AND PHARMACOKINETIC EVALUATION OF THE MICROCAPSULES ACCORDING TO THE INVENTION

EXAMPLE 1: PROTOCOLS FOR PHARMACOKINETIC AND BIOPHARMACEUTICS STUDIES

Six healthy subjects (6 men) were entered into each of the studies.Each subject had a satisfactory medical history with no evidence of diabetes, cardiovascular, hepatic, renal or gastro-intestinal disease.Each subject underwent a detailed medical screen which included haematology and blood biochemistry. All subjects were free from medication, including antacids and mild analgesics, for a period of one week prior to the study. No food or drinks, apart from water, were permitted from 10:00 p.m.before each study day until a period of 2 hours after receiving the dose of drug substance. Capsules of the test formulation were manufactured following Good Manufacturing Practices (GMP) and Good Clinical Practices (GCP) requirements. Tablets of the reference formulation were purchased in a pharmacy. Each subject received the two oral formulations in a balanced crossover design with one or two weeks between each treatment. The capsules and tablets were swallowed with water.

During the first 24 hours, blood samples (8 ml) were collected via an indwelling butterfly cannula intermittently flushed with heparinised solution, diluted 1:10 with sterile saline. There after samples were taken by direct venepuncture via the antecubital fossa. Direct venepuncture was used with some volunteers for all samples when the butterfly cannula caused discomfort.

Plasma samples were taken immediately predose, and at 0,5–1–1.5–2–3–4–6–8–10–12–16–24–36–48–72 and 96 hours after dosing. Each blood sample was immediately centrifuged at 4° C. to obtain plasma. The plasma was then stored at −20° C. in the dark until analysed for intact substance. Each of the plasma samples was analysed for unchanged drug substance.

EXAMPLE 2: ANALYSIS OF IN VIVO DISSOLUTION AND ABSORPTION

The evaluation of in vivo dissolution and absorption has been performed using indirect techniques involving the mathematical treatment of observed conventional plasma drug concentrations with time; indirect techniques discussed here were Wagner-Nelson or Loo-Riegelman analysis and deconvolution techniques (Umesh V.Banakar, Chetan D.Lathia and John H.Wood (1992). Interpretation of dissolution rate data and techniques of in vivo dissolution.In "Pharmaceutical Dissolution Testing", Marcel Dekker, Inc. New York, pp 189–249). The Wagner-Nelson or Loo-Riegelman techniques (Wagner Nelson is used for a one-compartment open model and Loo-Riegelman for a two-compartment open model) derived an equation to determine the input function. Numerical deconvolution not only provides the releaserate constant but also the release profile of the drug in the Gastro Intestinal (GI) tract from the solid dosage form.

The advantage of using deconvolution is that it describes both the fraction of dose reaching the systemic circulation and the time of dissolution. The plasma concentrations data were analysed using the "SIPHAR Package" written for an IBM PC compatible micro computer. Each of the plasma profiles of intact drug substance were fitted using an iterative program which minimised the sum of squares.For the oral profiles, a first order input (absorption) term was used, with either 1 or 2 exponential terms describing the decline of plasma levels (Equation 1). A reciprocal weighing factor was used throughout.

$$C_p = \sum_{i=1}^{n} C_i e^{-\lambda_i t} \quad 1$$

Where $C_p$ is the plasma concentration at time t, $C_i$ is the coefficient and $\lambda_i$ is the exponential constant for the nth term. A negative exponential term was used to describe the absorption phase. The maximum observed plasma levels ($C_{max}$) and the time that they were reached $T_{max}$ were taken directly from the analytical data.The area under the curve (AUC), determined either to the last measured time point or to infinite time, was calculated both by the trapezoidal rule (Yeh and Kwan, 1978) and by direct integration of the exponential equation.The half-life ($t_{1/2}$) of each of the decline phases of intact drug substance was obtained from equation 2 using the respective exponential constant from the curve fitting analysis.

$$t_{1/2} = \frac{0.693}{\lambda i} \quad 2$$

All parameters were automatically written into a file by the computer, together with the study code, for tabulation and statistical analysis. These in vivo data were analysed using the computer "SIPHAR Package" written for an IBM PC compatible micro-computer. The mean plasma profiles of intact drug substance following administration of controlled release microcapsules were used to determine the absorption profile of the fraction absorbed according to the WAGNER-NELSON and the deconvolution methods using ILL or WEIBUL equations and a POWELL algorithm.

EXAMPLE 3: ABSORPTION PROFILE OF A MICROENCAPSULATED FORMULATION OF ATENOLOL 3.1. PREPARATION OF ATENOLOL-CONTAINING MICROCAPSULES ACCORDING TO THE PRESENT INVENTION

The active ingredient, atenolol, used in the encapsulation procedure is in a powdery, microcrystalline form. The size distribution, as determined using a Coulter LS130 Granulometer with hexane as the solvent, gives the following results:

D(4, 3)=6,8 μm (D4,3=average diameter in volume), 80 weight percent of the sample with diameters between 1,1 and 14,7 μm.

Atenolol (2901 g) and PVP (86,8 g) and purified water (1953,5 g) were first mixed using a Lodige M5 GRI Granulator and then sieved to separate microparticles having a size between 200–315 μm (925 g). Purified water (199,6 g) was then sprayed onto the microparticles. In a Uniglatt Spray Coating Machine, 299,4 g of the sieved microparticles were then coated by spray drying. The coating solution which was used has the following composition:

| | |
|---|---|
| ethylcellulose | 44.7 g |
| PVP | 4.8 g |
| Castor Oil | 4.8 g |
| Magnesium Stearate | 6.1 g |
| aceton | 479.0 g |
| isopropanol | 53.0 g |
| salicylic acide | 15.1 g |

Sieving between 200 and 315 µm gives 202,8 gr of microcapsules whose characteristics are:

D(4,4)=272 µm,

80% of the mass is composed of microcapsules having a diameter between 198 µm and 355 µm;

percentage of active ingredient in the microparticle composition: 74 % atenolol.

3.2. IN VIVO ABSORPTION MEASUREMENT FOR SIX HEALTHY SUBJECTS AFTER ADMINISTRATION OF ATENOLOL MICROCAPSULES:

After administration of the product (100 mg) to man in a randomized cross over study versus tenormine (100 mg) and drawing of blood as explained in example 2, each of the plasma samples was analysed for unchanged atenolol. To each duplicate plasma sample or standard (1 ml), internal standard was added; both compounds were isolated from plasma by solid liquid extraction. Liquid chromatography was performed using an HP 1050 series system. Separation was conducted on a 15 cm×4 mm ID column packed with 4 µm superspher 100RP18, using a mobile phase of methyl alcohol/phosphate buffer (20/80; v/v) at a flow rate of 0.6 ml/min, with a fluorimetric detection. Under the conditions described for the analytical method, atenolol could be measured over a relatively long chromatogram time (30 min). The response was linear over the rane of 2.5–500 ng ml$^{-1}$. The minimum level of detection for intact atenolol was 2,5 ng.ml$^{-1}$ when using a 1 ml plasma sample. The means plasma levels [±Standard Deviations (SD)] of atenolol are presented in the following table 1 and in the enclosed FIG. 1.

TABLE 1

| Hours | Concentration in ng/ml |
|---|---|
| 0 | 0.00 ± 0.00 |
| 0.5 | 17.60 ± 14.01 |
| 1 | 89.07 ± 56.05 |
| 2 | 202.41 ± 88.71 |
| 3 | 488.02 ± 241.50 |
| 4 | 458.47 ± 133.51 |
| 6 | 296.52 ± 61.83 |
| 8 | 202.44 ± 45.95 |
| 10 | 146.03 ± 23.70 |
| 12 | 120.46 ± 20.57 |
| 16 | 74.03 ± 12.48 |
| 24 | 38.42 ± 6.87 |
| 36 | 14.32 ± 2.89 |
| 48 | 6.95 ± 2.35 |
| 72 | 0.88 ± 2.14 |
| 96 | 0.00 ± 0.00 |

From these results absorption analysis was performed using the WAGNER-NELSON and the deconvolution techniques.

Figure 2:
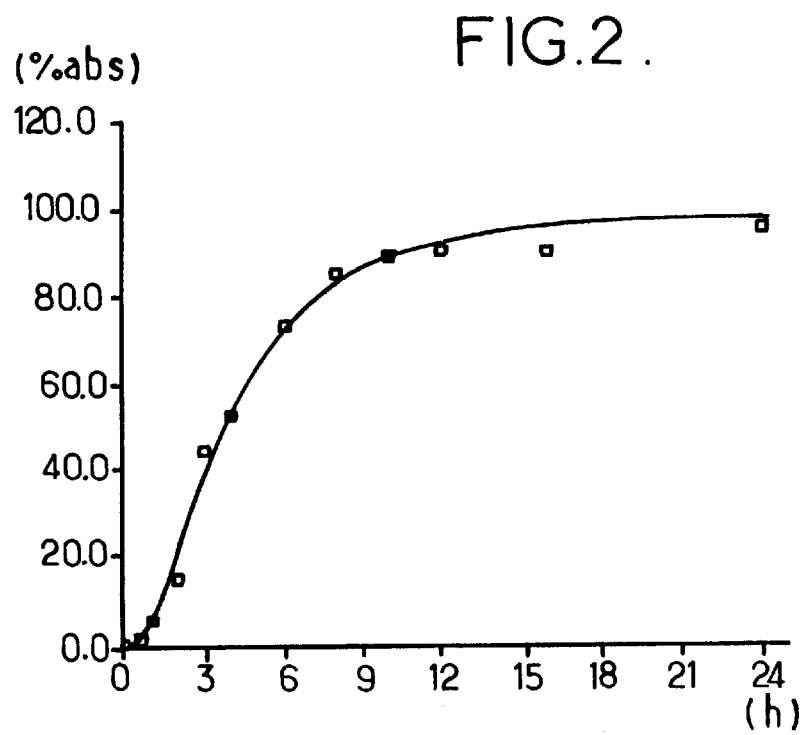
FIG. 2 shows the graph of atenolol in vivo cumulated absorption (percent absorbed), said absorption being performed using the WAGNER-NELSON and the deconvolution technics, as a function of time after the swallowing of the mnicrocapsules (example 3).

Both of these techniques allow to determine the times to reach 10,50 and 90,00% of drug absorbed as well as the mean absorption time Td and the shape curve parameter γ of the WEIBULL equations. Both techniques were used as the reference drug was a commercial tablet and not an I.V.administration. FIG. 2 shows the percent absorbed as a function of time. The respective parameters are presented below in table 2.

TABLE 2

| Parameters | WAGNER NELSON |
|---|---|
| $T_{10\%}$ | 1.51 hours |
| $T_{50\%}$ | 2.68 hours |
| $T_{90\%}$ | 22.84 hours |
| $T_D$ | 5.40 hours |
| γ | 0.83 hours |

The FIG. 2 shows that absorption prolongates itself beyond the usually admitted transit time in the small intestine, which is 3±1 hour. Thus, the galenical form according to the invention has a transit time superior to the physiological transit time, atenolol being not absorbed in the colon.

EXAMPLE 4: ABSORPTION PROFILE OF A MICROENCAPSULE FORMULATION OF ACYCLOVIR

4.1. PREPARATION OF ACYCLOVIR-CONTAINING MICROCAPSULES ACCORDING TO THE PRESENT INVENTION:

The active ingredient, acyclovir, used in the encapsulation procedure is in a powdery, microcrystalline form. The size distribution, as determined using a Coulter LS130 Granulometer with hexane as the solvent, gives the following results:

D(4,3)=8.6 µm, max. Diameter for 95 weight percent of the sample=28 µm.

Acyclovir (1500 g) and PVP (45 g) were first mixed with a solution of 50 w/50 w water-isopropanol (409 g) using a Bouvard Erweka Granulator and then sieved to separate granulates having a size between 315–500Iµm (973 g). In a Uniglatt Spray Coating Machine, the seived microparticles (350 g) were then coated by spray drying. The coating solution which was used has the following composition:

| | |
|---|---|
| ethylcellulose | 15.5 g |
| PVP | 1.7 g |
| Castor Oil | 1.7 g |
| Magnesium Stearate | 2.1 g |
| aceton | 166.0 g |
| isopropanol | 18.0 g |

The resultant microcapsules have the following characteristics:

D(4,3)=393 µm,

80% of the mass is composed of microcapsules having a diameter between 253 µm and 561 µm, percentage of active ingredient in the microparticle composition: 88% acyclovir.

Figure 3:
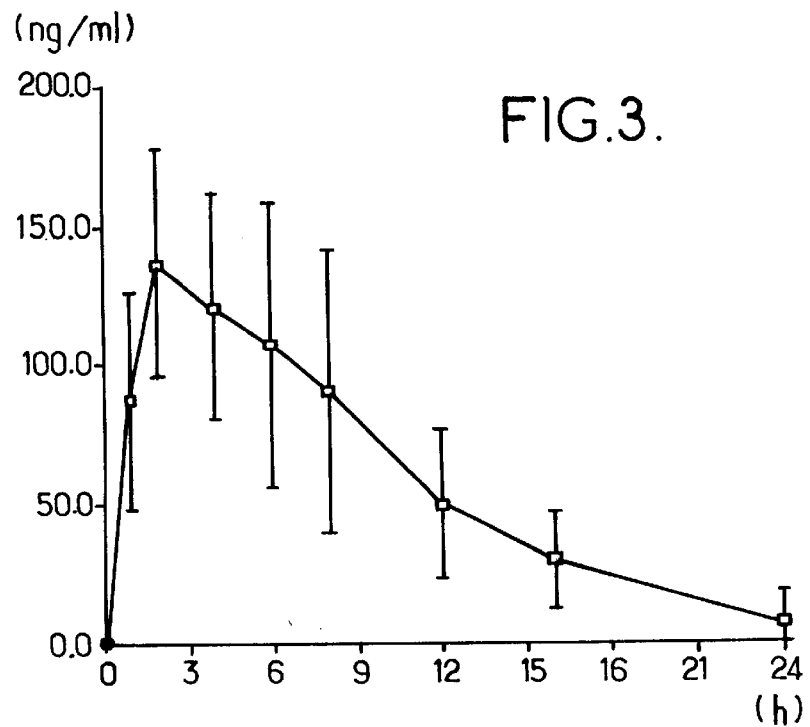
FIG. 3 shows the graph of the aciclovir plasma concentrations (ng/ml) as a function of time in hours (h) after the swallowing of the aciclovir (400 mg) microcapsules (example 4).

4.2. IN VIVO ABSORPTION MEASUREMENT FOR SIX HEALTHY SUBJECTS AFTER ADMINISTRATION OF ACYCLOVIR MICROCAPSULES:

After administration of the product to man (800 mg) of viropump acyclovir, in a randomized cross over study versus ZOVIRAX (200 mg) and drawing of blood as explained in example 2, aliquots of 1 ml plasma samples were mixed with 300 µl of 3M HClO$_4$ and agitated for 15 sec.on the Vortex mixer. The samples were then centrifuged for 5 min.and the clear supernatant transferred into an auto samples vial. 50 µl was injected into the BPLC system. Chromatographic separation was performed on a reversed phase C$_{18}$ column using a mobile phase made of acetonitril and 0,02M HClO$_4$ and the following gradient program: 100% HClO$_4$ for 5,9 min. 20% HClO$_4$, 80% acetonitril from 6 to 14 min, 100% HClO$_4$ from 14,1 min until the end of the analysis. Detection was achieved by fluorescence (λex: 260 nm, λem: 375 nm). Calibration curves range from 10 to 2000 ng/ml and the limits of quantification (L.O.Q) was set at 10 ng/ml. The validation of the method was assessed following the Good Laboratory Practices (GLP). The mean plasma levels (±SD) of aciclovir are presented in the following table 3 and in the enclosed FIG. 3.

| Hour | Concentration in ng/ml |
| --- | --- |
| 0 | 0.00 ± 0.00 |
| 0.5 | 50.00 ± 0.00 |
| 1 | 103.83 ± 39.44 |
| 2 | 128.03 ± 33.88 |
| 4 | 104.03 ± 13.08 |
| 6 | 56.3 ± 13.89 |
| 8 | 26.60 ± 21.14 |
| 12 | 4.08 ± 10.00 |
| 16 | 3.65 ± 8.94 |
| 24 | 3.78 ± 9.27 |

Figure 4:
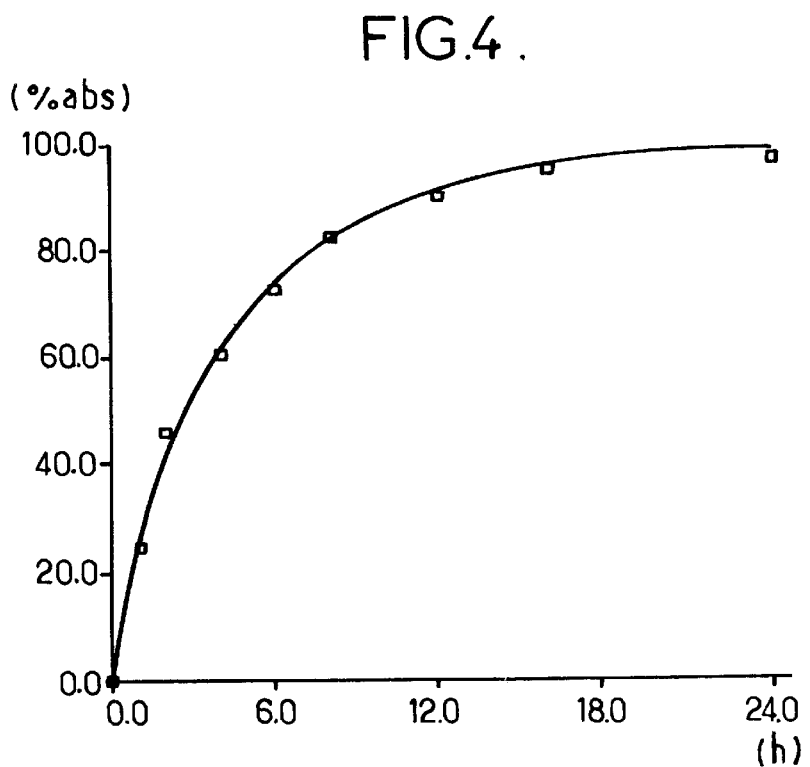
FIG. 4 shows the graph of aciclovir in vivo cumulated absorption (percent absorbed), said absorption being performed using the WAGNER-NELSON and the deconvolution technics, as a function of time after the swallowing of the microcapsules (example 4).

From these results absorption analysis was performed using the WAGNER-NELSON and the deconvolution techniques Both of these techniques allow to determine the times to reach 10,50 and 90% of drug absorbed as well as the mean absorption time Td and the shape curve parameter γ of the WEIBULL equations. Both techniques were used as the reference drug was a commercial tablet and not and I.V. administration. FIG. 4 shows the percent absorbed as a function of time. The respective parameter are presented below in table 4.

TABLE 4

| Parameters | Deconvolution |
| --- | --- |
| $T_{10\%}$ | 0.4 hours |
| $T_{50\%}$ | 2.60 hours |
| $T_{90\%}$ | 12.58 hours |
| $T_D$ | 4.04 hours |
| γ | 0.82 hours |

The FIG. 4 shows that absorption prolongates itself beyond the usually admitted transit time in the small intestine, which is 3±1 hour. Thus, the galenical form according to the invention has a transit time superior to the physiological transit time.

EXAMPLE 5: ABSORPTION PROFILE OF A MICROENCAPSULATED FORMULATION OF CAPTOPRIL

5.1. PREPARATION OF CAPTOPIRIL-CONTAINING MICROCAPSULES ACCORDING TO THE PRESENT INVENTION

The active ingredient, captopril, used in the encapsulation procedure is in a powdery, microcrystalline form. The size distribution, as determined using a Coulter LS130 Granulometer with hexane as the solvent, gives the following results:

D(4,3)=18 μm;

max. Diameter for 95 weight percent of the sample: 52,7 μm.

Captopril (2 800,6 g) and PVP (87,1 g) were first mixed with purified water (1 301 g) using a Lodige M5 GRI Granulator and then sieved to separate microparticles having a size between 200–315 μm (973 g). Purified water (200 g) was then sprayed onto the microparticles. In a Uniglatt Spray Coating Machine, 300 g of the sieved mnicroparticles were then coated by spray drying. The coating solution which was used has the following composition:

| | |
| --- | --- |
| ethylcellulose | 120.3 g |
| PVP | 13.0 g |
| Castor Oil | 13.0 g |
| Magnesium Stearate | 16.26 g |
| aceton | 1284.7 g |
| isopropanol | 142.7 g |

Sieving between 200 and 315 μm gives 57 g of microcapsules whose characteristics are:

D(4,3)=332 μm,

80% of the mass is composed of microcapsules having a diameter between 254 μm and 421 μm.

Percentage of active ingredient in the microparticle composition: 56,2% captopril.

5.2 IN VIVO ABSORPTION MEASUREMENT FOR SIX HEALTHY SUBJECTS AFTER ADMINISTRATION OF CAPTOPRIL MICROCAPSULES:

After administration of the product to man (100 mg) in a randomized cross over study versus lopril (100 mg) and drawing of blood as explained in example 2, plasma samples (100 μl) fortified with 50 ng of S-Benzyl Captopril as Internal Standard, was placed into screw-capped tube with 900 μl of water and 1 ml of 0,5 N-hydrochloric acid. After briefly stirring using a Vortex mixer, 5 ml of dichloromethane were added to each tube. The extraction procedure was conducted over a 15 minutes period using a shaker. The tubes were then centrifuged at 3 500 rpm for 5 minutes and the organic layer was transferred into a 10 ml glass tube and evaporated to dryness at 45° C. under nitrogen.

The residue was reconstituted in 1 ml of buffer pH=3 and the mixture was applied to $C_{18}$ disposable column previously conditioned with water and methanol. After a wash with water, the column was eluted with methanol (1 ml) and the eluate evaporated under a stream of nitrogen. To the residue were added 50 μl of an ethanolic solution, saturated with potassium carbonate and 50 μl of pentafluorobenzyl bromide solution at 1% in acetonitril. After 1,5 h of derivatisation at 80° C. the mixture was evaporated to dryness. To the residue were added 500 μl of acetonitril and a 2 μl sampling volume was injected into the gas chromatography mass spectrometer. The gas chromatography was carried on a fused-silica capillary column (8 m×0,25 mm) from chrompack wall coated with an O.V 1701 apolar stationary phase. The gas chromatographic conditions were the following:

oven initial temperature: 160° C.,

RATE/ 15° C./minute, oven final temperature: 280° C., transfer line: 280° C.,

The mass spectrometer was operated in the negative ion chemical ionisation mode using methane N45 as the reactant gas with an ion source pressure of about 0,5 Torr. The validation of the method was assessed following the Good Laboratory Practices (GLP).

Figure 5:
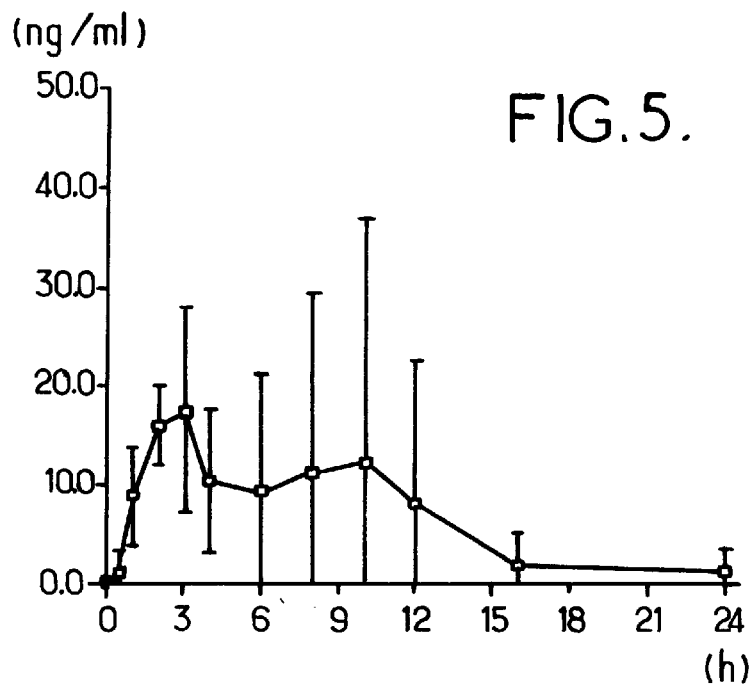
FIG. 5 represents the graph of the captopril plasma concentrations (ng/ml) as a function of time in hours (h) after the swallowing of the captopril (100 mg) microcapsules (example 5).

The mean plasma levels (±SD) of captopril are presented in the following table 5 and in the enclosed FIG. 5.

TABLE 5

| Hours | Concentration in ng/ml |
|---|---|
| 0 | 0.00 ± 0.00 |
| 0.5 | 0.93 ± 2.27 |
| 1 | 8.85 ± 5.15 |
| 2 | 16.05 ± 4.03 |
| 3 | 17.49 ± 10.51 |
| 4 | 10.40 ± 7.42 |
| 6 | 9.26 ± 12.03 |
| 8 | 11.25 ± 18.28 |
| 10 | 12.33 ± 24.50 |
| 12 | 8.00 ± 14.57 |
| 16 | 1.78 ± 3.21 |
| 24 | 1.31 ± 2.32 |
| 36 | 0.00 ± 0.00 |
| 48 | 0.00 ± 0.00 |
| 72 | 0.00 ± 0.00 |
| 96 | 0.00 ± 0.00 |

Figure 6:
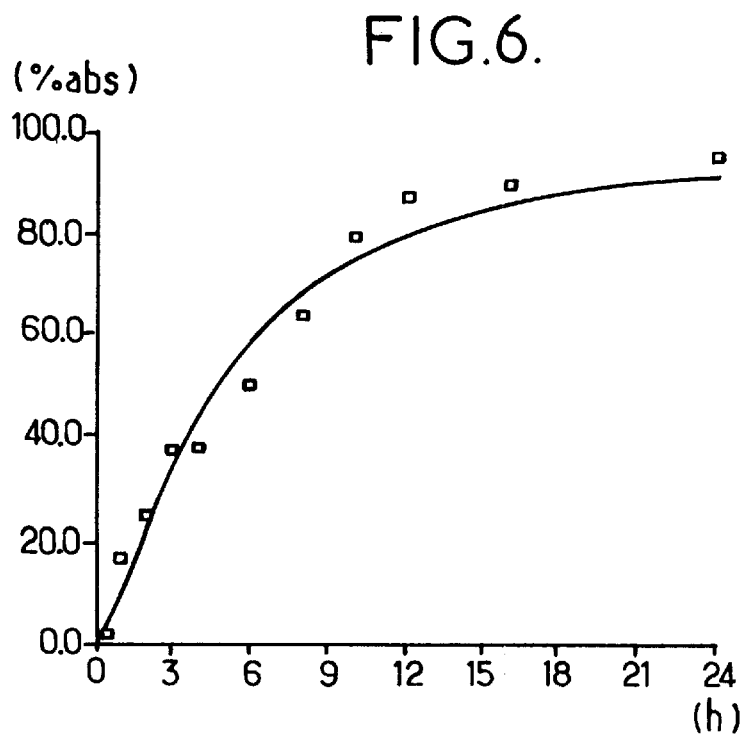
FIG. 6 shows the graph of captopril in vivo cumulated absorption (percent absorbed), said absorption being performed using the WAGNER-NELSON and the deconvolution technics, as a function of time after the swallowing of the microcapsules (example 5).

From these results absorption analysis was performed using the WAGNER-NELSON and the deconvolution techniques. Both of these techniques allow to determine the times to reach 10,50 and 90% of drug absorbed as well as the mean absorption time Td and the shape curve parameter γ of the WEIBULL equations. Both techniques were used as the reference drug was a commercial tablet and not an I.V. administration. FIG. 6 shows the percent absorbed as a function of time. The respective parameters are presented below in table 6.

TABLE 6

| Parameters | Deconvolution (hours) |
|---|---|
| $T_{10\%}$ | 0.78 |
| $T_{50\%}$ | 5.99 |
| $T_{90\%}$ | 16.54 |
| $T_D$ | 7.22 |
| γ | 1.04 |

The FIG. 6 shows that absorption prolongates itself beyond the usually admitted transit time in the small intestine, which is 3±1 hour. Thus, the galenical form according to the invention has a transit time superior to the physiological transit time.

EXAMPLE 6: ABSORPTION PROFILE OF A MICROENCAPSULATED FORMULATION OF CIMETIDIN 6.1. PREPARATION OF CIMETIDIN-CONTAINING MICROCAPSULES ACCORDING TO THE PRESENT INVENTION:

The active ingredient, cimetidin, used in the encapsulation procedure is in a powdery, microcrystalline form. The size distribution, as determined using a Coulter LS130 Granulometer with hexane as the solvent, gives the following results:

D(4, 3)=19.8 μm, 80 weight percent of the sample with diameters between 1,8 and 41,4 μm. Cimetidin (2 899,8 g) and PVP (88,9 g) were first mixed with purified water (1 039,2 g) using a Lodige M5 GRI Granulator and then sieved to separate microparticles having a size between 200–315 μm (907 g). 198,3 g of purified water were then sprayed onto the microparticles.

In a Uniglatt Spray Coating Machine, 299,8 g of the sieved microparticles were then coated by spray drying. The coating solution which was used has the following composition:

| ethylcellulose | 54.40 g |
|---|---|
| PVP | 5.90 g |
| Castor Oil | 5.90 g |
| Magnesium Stearate | 7.37 g |
| aceton | 580.00 g |
| isopropanol | 64.40 g |
| salicylic acid | 18.40 g |

Sieving between 200 and 315 μm gives 60 gr of microcapsules whose characteristics are:

D(4,3)=308 μm

80% of the mass is composed of microcapsules having a diameter between 219,4 μm and 413,4 μm.

Percentage of active ingredient in the microparticle composition : 64% cimetidin.

Figure 7:
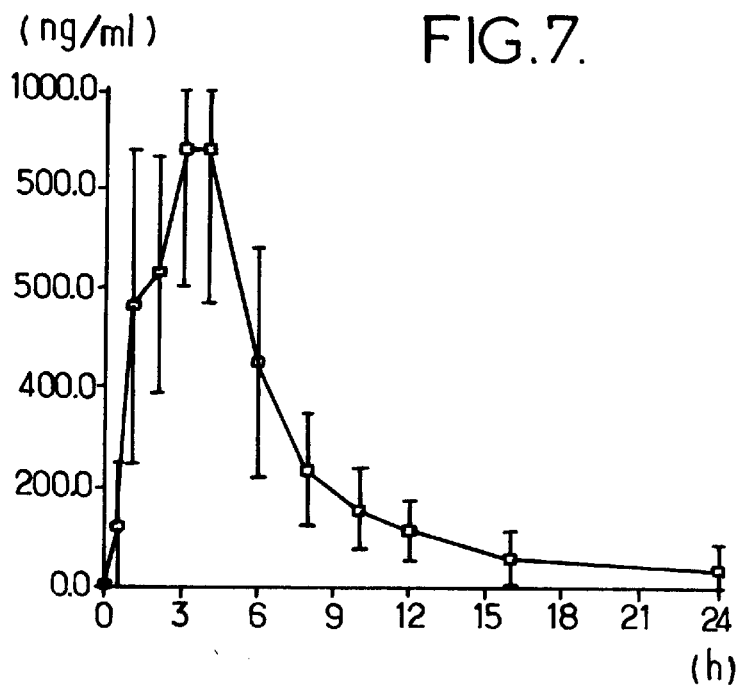
FIG. 7 shows the graph of the cimetidin plasma concentrations (ng/ml) as a function of time in hours (h) after the swallowing of the cimetidin (800 mg) microcapsules (example 6).

6.2. IN VIVO ABSORPTION MEASUREMENT FOR SIX HEALTHY SUBJECTS AFTER ADMINISTRATION OF CIMETIDIN MICROCAPSULES:

After administration of the product to man (800 mg) in a randomized cross over study versus TAGAMET (800 mg) and drawing of blood as explained in example 2, an aliquot of 0,5 ml of plasma sample was passed through a C18 Bond Elut extraction cartridge conditioned by 1 ml of methanol and 1 ml of ultra pure water. After washing by 1 ml of water, the sample was eluted with 1 ml of HPLC mobile phase, 10 μl of internal standard solution (200 μg/ml procainamide in water) was then added and 50 μl was injected into the HPLC system. Chromatographic separation was performed on a Macherey Nagel Spherisorb 80-3 CN 3 μm 125×8×4 mm I. D. column using a mobile phase made of acetonitril and 5 mM pH 5 phosphate buffer (50/50, v/v). Detection was achieved by UV spectrophotometric detection at 220 nm. Calibration standards were prepared in bulk by spiking a constant volume of biological fluid to be assayed with known and increasing amounts of cimetidin. An aliquot of these standards was then treated exactly in the same way as the samples to be assayed. The concentration levels were: 0,05–0,1–0,2–0,5–1–2–5–10 μg/ml. Concentrations of cimetidin in the study samples were calculated using a calibration curve constructed daily. Responses were obtained as the peak height ratios of cimetidin to internal standard. The curve was not forced through zero (resp=a °C+b) and a weighting factor of $I/C^2$ was applied as described in the assay method. The limit of detection (LOD) was estimated to be 0.025 μg/ml and the limit of quantification (LOQ) was 0,05 μg/ml. The mean plasma levels (±SD) of cimetidin are presented in the following table 7 and in the enclosed FIG. 7.

TABLE 7

| Hours | Concentration in ng/ml |
|---|---|
| 0.0 | 0.00 ± 0.00 |
| 0.5 | 119.83 ± 133.01 |
| 1 | 565.00 ± 317.51 |
| 2 | 630.17 ± 239.82 |
| 3 | 884.17 ± 281.23 |
| 4 | 882.67 ± 311.78 |
| 6 | 453.67 ± 230.47 |
| 8 | 237.67 ± 115.01 |
| 10 | 156.83 ± 83.55 |
| 12 | 117.17 ± 63.57 |
| 16 | 59.17 ± 53.82 |
| 24 | 39.17 ± 50.55 |

TABLE 7-continued

| Hours | Concentration in ng/ml |
|---|---|
| 36 | 10.33 ± 25.31 |
| 48 | 0.00 ± 0.00 |
| 72 | 0.00 ± 0.00 |
| 96 | 0.00 ± 0.00 |

Figure 8:
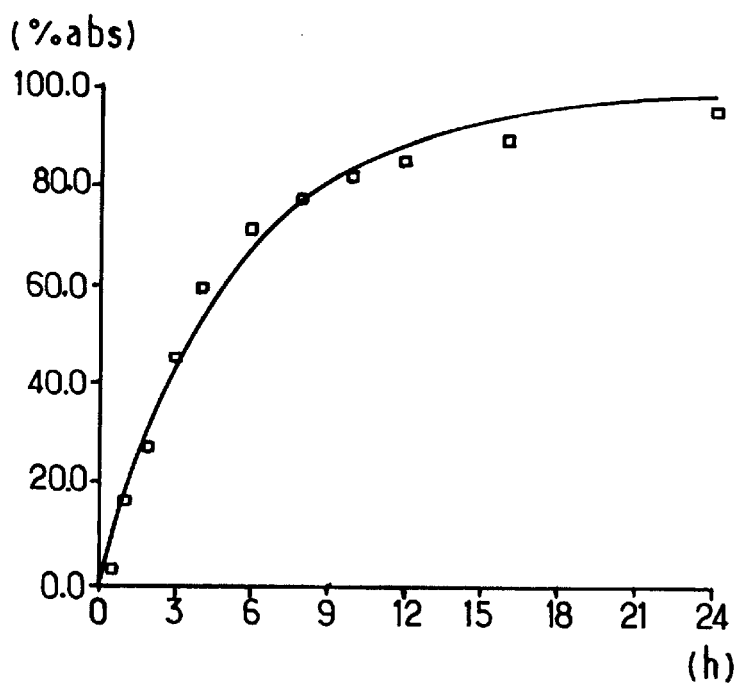
FIG. 8 shows the graph of cimetidin in vivo cumulated absorption (percent absorbed), said absorption being performed using the WAGNER-NELSON and the deconvolution technics, as a function of time after the swallowing of the microcapsules (example 6).

From these results absorption analysis. Absorption analysis was performed using the WAGNER-NELSON and the deconvolution techniques. Both of these techniques allow to determine the times to reach 10,50 and 90,00% of drug absorbed as well as the mean absorption time Td and the shape curve parameter $\gamma$ of the WEIBULL equations. Both techniques were used as the reference drug was a commercial tablet and not an I.V. administration. FIG. 8 shows the percent absorbed as a function of time. The respective parameter are presented below in table 8.

TABLE 8

| Parameters | Deconvolution (hours) |
|---|---|
| $T_{10\%}$ | 0.76 |
| $T_{50\%}$ | 3.33 |
| $T_{90\%}$ | 16.94 |
| $T_D$ | 5.39 |
| $\gamma$ | 0.96 |

The FIG. 8 shows that absorption prolongates itself beyond the usually admitted transit time in the small intestine, which is 3±1 hour. Thus, the galenical form according to the invention has a transit time superior to the physiological transit time, cimetidin being not absorbed in the colon.

We claim:

1. Microcapsules of reservoir kind containing at least one medicinal nd nutritional active principle (AP), with the exclusion of acetylsalicylic acid (ASA), which are intended for oral administration, characterized:

in that they consist of particles of AP each coated with at least one coating film of specific following composition:

1- at least one film-forming polymer (P1) which is insoluble in the liquids of the digestive tract, present in a quantity of 50 to 90%, preferably 50 to 80% by weight of dry matter of the whole coating composition, and consisting of at least one non-hydrosoluble cellulose derivate, ethylcellulose and/or cellulose acetate being prefered;

2- at least one nitrogen-containing polymer (P2), present in a quantity of 2 to 25, preferably 5 to 15% by weight of dry matter of the whole coating composition, and consisting of at least one polyacrylarnide and/or one poly-N-vinylamide and/or one poly-N-vinyl-lactame, the polyacrylamide and/or the polyvinylpyrrolidone being prefered;

3- at least one plasticizer present in a quantity of 2 to 20%, preferably 4 to 15% by weight of dry matter of the whole coating composition, and consisting of at least one of the following compounds: glycerol esters, phtalates, citrates, sebacates, cetylalcohol esters, castor oil and cutin, castor oil being particularly prefered;

4- at least one surface-active and/or lubricating agent, present in a quantity of 2 to 20%, preferably 4 to 15% by weight of dry matter of the whole coating composition, and chosen from anionic surfactants, preferably the alkali metal or alkakine-earth metal salts of fatty acids, stearic acid and/or oleic acid being preferred, and/or from nonionic surfactants, preferably polyoxyethylenated esters of sorbitan and/or polyoxyethylenated esters of sorbitan and/or polyoxyethylenated derivatives of castor oil, and/or from lubricants such as stearates, preferably calcium, magnesium, aluminium or zinc stearate, or such as stearylfumarate, preferably sodium stearylfimarate, and/or glyceryl behenate, said agent comprising only one or a mixture of the above products;

in that they have a particle size of between 50 and 1000 microns, preferably of between 100 and 750 microns and, more preferably, of between 100 and 500 microns;

in that they are designed so as to be able to remain in the small intestine for a period of at least about 5 hours, preferably of at least about 7 hours and, even more preferably, for a period of between about 8 hours and about 24 hours, and permitting so the absorption of the AP during at least part of their residence in the small intestine.

2. Microcapsules according to claim 1, characterized in that they comprise an amount of AP of between 55 and 95% by weight, and preferably of between 70 and 85% by weight.

3. Microcapsules according to claim 1, characterized in that the coating composition comprises from 60 to 80% of ethylcellulose, from 5 to 10% of polyvinylpyrrolidone, from 5 to 10% of castor oil and from 2 to 8% of magnesium stearate.

4. Microcapsules according to claim 1, characterized in that they are mixed with 0,5 to 5% by weight, preferably 1,5 to 3% by weight, of at least one anti-agglomerating agent formed, preferably, of talc, colloidal silica or of a mixture of the two.

5. Microcapsules according to claim 1, characterized in that the AP used belongs to at least one of the following families of active substances: antiulcer, antidiabetic, anticoagulant, antithrombic, hypolipaemic, antiarrhythmic, vasodilatory, antianginal, antihypertensive, and vasoprotective agents, fertility enhancers, labour inducers and inhibitors, and contraceptive, antibiotic, antifingal, antiviral, anticancer, anti-inflammatory, analgesic, antiepileptic, antiparkinsonian, neuroleptic, hypnotic, anxiolytic, psychostimulatory, antimigraine, antidepressant, antitussive, antihistamine or antiallergic agents.

6. Microcapsules according to claim 5, characterized in that AP is chosen from the following compounds pentoxifyllin, prazosin, acyclovir, nifedipin, diltiazem, naproxen, ibuprofen, flurbiprofen, ketoprofen, fenoprofen, indomethacin, diclofenac, fentiazac, oestradiol valerate, metoprolol, sulpiride, captopril, cimetidin, zidovudin, nicardipine, terfenadine, atenolol, salbutamol, carbamazepin, ranitidine, enalapril, simvastatin, fluoxetin, alprazolam, famotidin, ganciclovir, famiciclovir, spironolacton, 5-asa, quinidin, perindopril, morphin, pentazocin, paracetamol, omeprazol, metoclopraniid and mixtures thereof.

7. Microcapsules according to claim 1, characterized in that the AP consists of at least one nutritional and/or dietary supplement, preferably chosen from vitamins, amino acids, trace elements, antioxidants and mixtures thereof.

8. Process for producing the microcapsules according to claim 1, characterized in that it consists essentially in:

a/ selecting, or in case of need making, microparticles of AP with a particle size of between 50 and 1000 microns, preferably of between 100 and 750 microns and, even more preferably, of between 100 and 500 microns, b/ preparing the coating composition by mixing together a polymer P1, a polymer P2, the plasticizer and the surface active and/or lubricating agent in a solvent system c/ applying the coating composition/solvent system mixture to particles of AP, d/ drying the microcapsules thus obtained, and e/ optionally, mixing these microcapsules with at least one anti-agglomerating agent.

9. Process according to claim 7, characterized in that the solvent system is formed by compounds selected from the following list: ketones, esters, chlorinated solvents, alcohols, which are preferably aliphatic, alkanes and mixtures thereof:

the compounds containing from 1 to 6 carbons being preferred, and acetone, methyl ethyl ketone, methanol, ethanol, isopropanol and methylene chloride being particularly preferred.

10. Process according to claim 7, characterized in that the coating composition/solvent system mixture is applied by spraying onto the articles of AP set in motion, preferably by mechanical stirring or by fluidization.

11. Method of preparation of pharmaceutical forms, preferably in the form of tablets that can advantageously be crumbled, or powders or gelatin capsules, wherein the improvement is the use of the microcapsules according to claim 1.

12. Galenical system containing the microcapsules according to claim 1.

13. Method for treating and/or preventing diseases and/or pains, consisting in using the microcapsules according claim 1.

14. A method for treating and/or preventing diseases and/or pains, which comprises using microcapsules as a vehicle for at least one medicinal, nutritional or combination thereof as Active Principle (AP) which is capable of remaining in the small intestine for a prolonged period, said microcapsules:

being designed for oral administration and so as:

to be able to remain in the small intestine for at least about 5 hours, preferably at least about 7 hours and, even more preferably, for a period of between 8 and 24 hours, and to make it possible to release the AP in the small intestine during at least part of their residence, and consisting of particles of AP each coated with at least one coating film of specific composition and having a particle size of between 50 and 1000 $\mu$m, preferably of between 100 and 750 $\mu$m and, even more preferably, of between 200 and 500 $\mu$m.

* * * * *